United States Patent [19]
Lewis

[11] Patent Number: 5,337,595
[45] Date of Patent: Aug. 16, 1994

[54] SUBSONIC VENTURI PROPORTIONAL AND ISOKINETIC SAMPLING METHODS AND APPARATUS

[75] Inventor: Gary W. Lewis, Fountain Valley, Calif.

[73] Assignee: Horiba Instruments, Incorporated, Irvine, Calif.

[21] Appl. No.: 853,506

[22] Filed: Mar. 18, 1992

[51] Int. Cl.$^5$ .................................. G01N 1/22
[52] U.S. Cl. ............................... 73/23.31; 73/863.01
[58] Field of Search ............. 73/23.31, 23.32, 23.33, 73/863.01, 863.02, 853.03, 863.58, 863.86, 863.83

[56] References Cited

U.S. PATENT DOCUMENTS

| | | | |
|---|---|---|---|
| 3,593,023 | 7/1971 | Dodson et al. | 73/863.12 |
| 3,603,155 | 9/1971 | Morris et al. | 73/863.01 |
| 3,699,814 | 10/1972 | Kaufman | 73/863.11 |
| 3,784,902 | 1/1974 | Huber | 73/863.03 |
| 3,817,100 | 6/1974 | Anderson et al. | 73/861.63 |
| 3,965,749 | 6/1976 | Hadden et al. | 73/23.31 |
| 4,586,367 | 5/1986 | Lewis | 73/23.33 |
| 4,660,408 | 4/1987 | Lewis | 73/863.12 |
| 4,823,591 | 4/1989 | Lewis | 73/3 |
| 5,184,501 | 2/1993 | Lewis et al. | 73/23.31 |

*Primary Examiner*—Hezron E. Williams
*Assistant Examiner*—Nashmiya Ashraf
*Attorney, Agent, or Firm*—Harness, Dickey & Pierce

[57] ABSTRACT

Subsonic venturi proportional and isokinetic sampling methods and apparatus for use in evaluating exhaust emissions from an exhaust source which utilizes a pair of calibrated subsonic venturi restrictions for measuring the bulkstream and extracted sample flow rates respectively. The subsonic venturis may be specifically configured relative to each other to provide isokinetic sampling under specified control conditions.

9 Claims, 1 Drawing Sheet

SUBSONIC VENTURI PROPORTIONAL AND ISOKINETIC SAMPLING METHODS AND APPARATUS

BACKGROUND OF THE INVENTION

This invention relates to subsonic venturi proportional and isokinetic sampling methods and an apparatus, and more particularly to an arrangement for determining the gaseous constituents of exhaust utilizing a pair of subsonic venturi restrictions, one for measuring the exhaust or exhaust/air flow and the other for measuring the flow of an extracted sample, wherein the system is designed to provide both proportional and proportional isokinetic sampling.

Under present day federal regulations, the exhaust emissions from motor vehicles must not exceed specified values of certain constituent contaminants, as set forth in the Code of Federal Regulations. See, for example, Title 40 of the Code of Federal Regulations, parts 81–99, subparts A, B, D, E, F, G, K and N. See also Kaufman, U.S. Pat. No. 3,699,814. The presence of such standards has made it imperative that the exhaust emissions from vehicle engines be tested and analyzed to determine the relative amount of certain constituents therein. Much effort has gone into the development of equipment for use in this field of exhaust gas sampling, and it is now known to deliver exhaust from an internal combustion engine at an accurately controlled flow rate through a test apparatus for purposes of determining and analyzing the relative amounts of constituents therein. The general scheme of such testing is to add dilution air to the exhaust. The total volume of the mixture of exhaust and dilution air must be measured. A continuously proportional sample of volume must be collected and is stored for subsequent analysis of constituents such as hydrocarbons, carbon monoxide and $NO_x$. Mass emissions are determined from the sample concentrations and total flow over the test period.

Once such system for analyzing samples from exhaust gases is set forth in U.S. Pat. No. 3,699,814 to Kaufman entitled, "Gas Sampler," issued Oct. 24, 1972. The disclosure of this patent is incorporated herein by reference. The Kaufman patent is directed to a gaseous exhaust emission sampler which replaced the constant displacement pump of prior systems with a critical flow venturi and centrifugal blower for metering the diluted exhaust emissions at a constant volume flow.

Another system utilizes a pair of critical flow venturis for proportional sampling. An example of such a system is set forth in U.S. Pat. No. 3,817,100. In another such system, a downstream pump produces a sufficient vacuum on the bulkstream critical flow venturi exit so that the bulkstream mixture is flowing at sonic velocity, a condition which limits the bulkstream mixture to a constant mass flow rate at a given set of upstream temperature and pressure conditions measured at the bulkstream critical flow venturi inlet. A sample is extracted from the dilute bulkstream flow through another critical flow venturi in close proximity to the bulkstream critical flow venturi so that the venturis are operating under the same inlet pressure and temperature conditions. This sample critical flow venturi operates in connection with a downstream pump in the sampling line to create sonic flow, and thereby a constant mass flow rate at the measured upstream temperature and pressure conditions. Thus, the sample critical flow venturi extracts a sample for analysis at a flow rate proportional to the bulkstream flow rate.

Although this type of proportional sampling system using two critical flow venturis has certain advantages, it has a disadvantage in that it does not provide for active control of the bulkstream or sample flow rates to allow static and dynamic sampling of the bulkstream mixture. Consequently, such prior art systems cannot readily accommodate the testing of different size internal combustion engines which generate substantially different exhaust flow volumes without using different bulkstream critical flow venturis.

It is, therefore, a principal object of this invention to provide improved methods and an apparatus for sampling the emission content of exhaust from an exhaust source which provides for active flow control and proportional sampling, and may be sized for isokinetic flow conditions.

It is another object of this invention to provide methods and an apparatus for sampling the emission content of exhaust from an exhaust source which utilizes a pair of subsonic venturi restrictions that have substantially the same throat pressure for a preselected ratio of the flow rate of the exhaust to the flow rate of the extracted sample through their respective venturi throats, providing proportional sampling.

SUMMARY OF THE INVENTION

A first embodiment of this invention is adapted to be embodied in an apparatus for sampling the emission content of exhaust from an exhaust source comprising an exhaust inlet adapted for connection with the exhaust source. A flow establishing device is coupled with a flow confining path for establishing a flow of the exhaust from the exhaust source in the flow confining path. The apparatus further includes means for measuring the flow rate of the exhaust including a first subsonic venturi restriction and means for measuring the flow rate of an extracted sample of the exhaust which includes a second subsonic venturi restriction. Means are also provided for controlling the flow rate of the exhaust through the first subsonic venturi restriction and the flow rate of the extracted sample through the second subsonic venturi restriction for obtaining proportional sampling. In accordance with another feature of this embodiment, the first and second subsonic venturi restrictions are configured to have substantially the same throat pressure for a predetermined ratio of the flow rate of the exhaust through the throat of the first subsonic venturi restriction to the flow rate of the extracted sample through the throat of the second subsonic venturi restriction.

In another embodiment of the invention, a method for sampling the emission content of exhaust from an exhaust source is provided. This method comprises the steps of establishing a flow of exhaust in a flow confining path, measuring the flow rate of the exhaust using a first subsonic venturi restriction, measuring the flow rate of an extracted sample of the exhaust using a second subsonic venturi restriction, and controlling the flow rate of the exhaust through the first subsonic venturi restriction and the flow rate of the extracted sample through the second subsonic venturi restriction to obtain proportional sampling. In accordance with another feature of this embodiment, the method further includes the step of maintaining substantially the same throat pressure in the first and second subsonic venturi restrictions for a predetermined ratio of the flow rate of the exhaust through the throat of the first subsonic venturi restriction to the flow rate of the extracted sample through the throat of the second subsonic venturi restriction.

DETAILED DESCRIPTION OF THE PREFERRED EMBODIMENTS OF THE INVENTION

Figure 1:
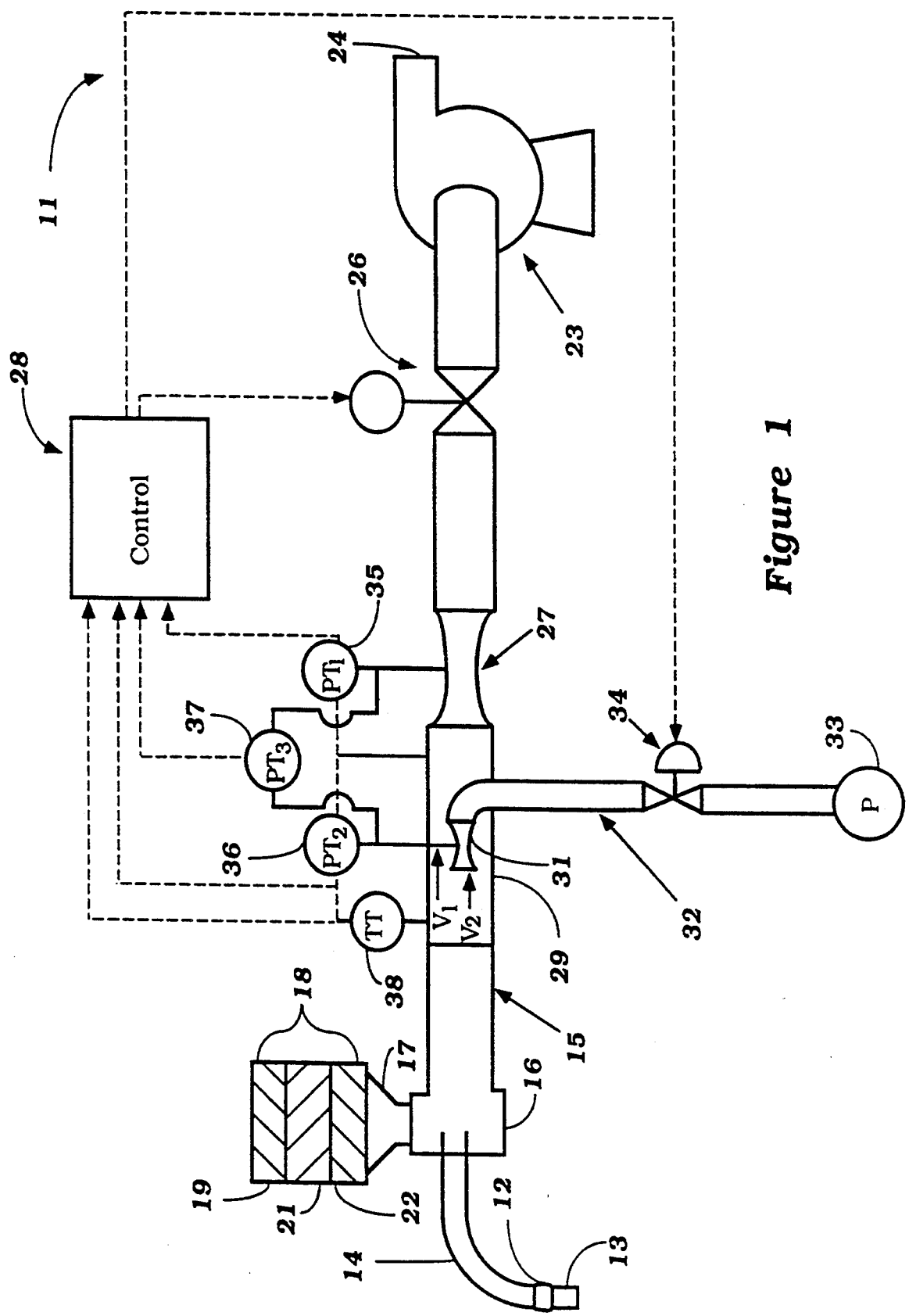
FIG. 1 is a diagrammatic illustration of a subsonic venturi proportional and isokinetic sampling apparatus constructed in accordance with embodiments of the invention.

Referring to FIG. 1 of the drawings, a subsonic venturi proportional sampling apparatus for sampling and measuring the emission content of exhaust from a source is depicted and is identified generally by the reference numeral 11. The apparatus 11 comprises a tail pipe adapter 12 for coupling to an internal combustion engine exhaust tail pipe 13. Exhaust from the tail pipe 13 is introduced through an exhaust inlet pipe 14 into a primary fluid flow confining path or line, designated generally by the reference numeral 15.

The primary flow confining path 15 may include at its upstream end near its connection with inlet pipe 14 a mixing duct 16 which is coupled to an air stack 17 that receives ambient inlet air through a filter assembly 18. This filter assembly 18 may be implemented using a series of stacked filters such as a pre-filter 19, a charcoal filter 21 and an absolute filter 22. When used, the filter assembly 18 serves generally to provide a supply of relatively pollution-free inlet air which is mixed in the mixing duct 16 with the exhaust from the internal combustion engine or other exhaust source coupled to the exhaust inlet pipe 14 to provide an exhaust/inlet dilution air mixture which flows through the primary flow confining path 15.

A compressor unit or pump 23 is coupled in the primary flow path 15 and provides vacuum pressure to establish the flow of the mixture or exhaust, sometimes referred to herein as the bulkstream flow, in the primary flow path 15. The flow establishing compressor unit or pump 23 vents to the atmosphere through a discharge vent 24.

An adjustable flow control valve 26 upstream of the pump 23 is provided for controlling the bulkstream flow rate through a calibrated subsonic venturi restriction 27 which is used for measuring the bulkstream flow rate. The flow control valve 26 is electrically connected to a control unit 28, which may be a digital or analog computer, for automatic adjustment of the bulkstream flow rate. Although computer controlled adjustment is preferred, the system may alternatively be arranged so that the valve 26 is manually adjusted.

The control valve 26 may be eliminated if a variable speed compressor, turbocompressor, or variable speed positive displacement pump is used as the flow establishing means in place of a single speed compressor or pump 23. In this case, the variable speed pump, compressor or turbocompressor preferably will be electrically connected to the control unit 28 for automatic adjustment of the bulkstream flow rate.

It should be noted that the flow rates referred to herein with respect to the present invention are mass flow rates.

In operation, a sample of the exhaust or mixture is extracted from a sampling zone 29 in the primary flow path 15 by another calibrated subsonic venturi restriction 31 and flows through a sample flow path or line 32. A pump 33 provides a sufficient vacuum in the sample line 32 to establish sample flow through the subsonic sample venturi 31 into line 32. An adjustable flow control valve 34 is positioned in the sample flow path 32 upstream of the pump 33 to regulate the sample flow rate through the sample line 32 and the subsonic sample venturi 31 which is used to measure the sample flow rate. This valve 34 along with the valve 26 or variable speed flow establishing means are controlled so that the flow rate of the extracted sample is proportional to the flow rate of the bulkstream flow so as to obtain proportional sampling.

The bulkstream flow rate is obtained using a pressure transducer 35 which measures the pressure difference between the sampling zone 29 upstream of the inlet of venturi 27 and the pressure at the throat of the venturi restriction 27, and a temperature transducer 38 and pressure transducer 39 which measure the temperature and pressure respectively upstream of the venturi 27. The extracted sample flow rate is obtained using a pressure transducer 36 which measures the pressure difference between the sampling zone 29 and the pressure at the throat of the venturi restriction 31, and the temperature transducer 38 and pressure transducer 39 which measure the temperature and pressure respectively upstream of the venturi 31.

These transducers 35, 36, 38 and 39 are each electrically connected to the computer control unit 28 and are each adapted to transmit electrical signals to the control unit 28 indicative of the measured pressure or temperature conditions. The control unit 28 then computes the bulkstream flow rate and sample flow rate through their respective venturis 27 and 31 based on the signals received from these transducers 35, 36, 38 and 39 and from the individual calibration data of the venturis 27 and 31, which have been previously calibrated and the data stored in the control unit 28, in accordance with well known equations. The bulkstream and sample flow rates through the venturis 27 and 31 respectively are computed on a continuous basis so that the computer control unit 28 may monitor the flow rates and transmit electrical signals to the valve(s) 26 and/or 34 to adjust the bulkstream and/or extracted sample flow rates so as to maintain the desired flow rate ratio which may be slightly altered during a testing period by fluctuations in the system.

In accordance with other features of the invention, the calibrated subsonic venturi restrictions 27 and 31 are designed so that they have the same pressures in their throats, measured by the pressure transducers 35 and 36 respectively, at a desired ratio of the flow rate through bulkstream subsonic venturi 27 to the flow rate through sample subsonic venturi 31. In this case, the cross-sectional areas exposed to the bulkstream or sample flow of the subsonic venturi restrictions 27 and 31 are preferably designed and configured so that the ratio of the cross-sectional throat area of venturi 27 to the cross-sectional throat area of venturi 31 equals the ratio of the flow rate through venturi 27 to the flow rate through venturi 31. When these design configurations are incorporated, the apparatus 11 may be operated to provide proportional isokinetic sampling wherein $V_1$ (the bulkstream flow velocity in sampling zone 29) and $V_2$ (the sample flow velocity at the inlet of venturi 31) are equal.

Isokinetic sampling is a particular type of proportional sampling and may generally be described as the extraction of a representative sample at the same gas velocity as the non-extracted gas such that the process does not disturb the gas flow, resulting in a more representative sample that is not effected by the method of extraction, such as particulate sample measurements. Under proportional isokinetic sampling conditions, the ratio of the flow rate through venturi 27 to the flow rate through venturi 31 is typically one hundred-to-one. However, other flow rate ratios may also be used to provide proportional isokinetic sampling depending on the specific design configurations of the venturis 27 and 31.

Moreover, in a system in which the ideal flow rate is one hundred-to-one for proportional isokinetic sampling, flow rates such as seventy-five-to-one or fifty-to-one may be used. In this instance, the system will only approximate isokinetic sampling but will provide proportional sampling.

For proportional isokinetic sampling a differential pressure transducer 37 is used to monitor the pressure difference between the throats of the venturis 27 and 31. If a pressure difference is measured by the pressure transducer 37, a correction signal is transmitted by the transducer 37 to the control unit 28 which, in turn, monitors and controls the pressure differential. When it receives the correction signal, the control unit 28 transmits a signal to the control valve 34 to adjust the sample flow rate through subsonic venturi restriction 31 to null the pressure difference signal so that the pressure transducer 37 is maintained at minimum value (i.e., zero) to maintain the desired flow rate ratio. Pressure transducer 37 may be chosen with a more sensitive operating range than pressure transducers 35 and 36 to provide a higher amplitude correction signal.

By using two subsonic venturis, one 27 for the bulkstream flow and the other 31 for the sample flow, which may be operated over a range of flow rates, adjustable and proportional sampling may be achieved. In a particular case, the geometries of bulkstream subsonic venturi 27 and sampling subsonic venturi 31 may be arranged such that the velocities of the bulkstream and sample flow rates are equal, thereby providing isokinetic sampling conditions. In addition to proportional and isokinetic sampling, active flow control is also provided.

It should be noted that if the air stack assembly 18 is not used, a raw exhaust sample may be extracted which is then diluted in the sample line 32. In this case, a filter may be located in the sample path 32 upstream of the flow control valve 34 to remove particulates from the raw exhaust. In addition, a dry gas supply line may be coupled to the sample line 32 upstream of the flow control valve 34 and filter. The flow rate of the dry gas which is used to dilute the extracted raw sample may be regulated by a mass flow meter that is coupled in the dry gas line. An example of a system wherein no air stack is used and instead a raw exhaust sample is extracted and diluted in the sample line is set forth in the application entitled "Exhaust Sampler And Control Means," U.S. Ser. No. 695,606, filed May 3, 1991 in the names of Gary W. Lewis et al. and assigned to the assignee of this application. The disclosure of this application is incorporated herein by reference.

It should be readily apparent from the foregoing description that a highly effective exhaust proportional sampling apparatus for sampling the emission content of exhaust from an exhaust source, as well as proportional sampling methods, have been illustrated and described. Using a pair of calibrated subsonic venturis and the controls associated with the apparatus, a desired flow rate ratio of the exhaust or bulkstream flow rate to the sample flow rate may be maintained so as to obtain proportional sampling. The subsonic venturis may also be specifically configured and operated to achieve isokinetic sampling, wherein the exhaust flow velocity and sample flow velocity are equal. Although embodiments of the invention have been illustrated and described, various changes and modifications may be made without departing from the spirit and scope of the invention, as defined by the appended claims.

I claim:

1. An apparatus for sampling the emission content of exhaust from an exhaust source comprising an exhaust inlet adapted for connection with the exhaust source, a flow confining path for the exhaust from the exhaust source, a flow establishing device coupled with said flow confining path for establishing a flow of the exhaust in said flow confining path, means for measuring the flow rate of the exhaust comprising a first subsonic venturi restriction, means for extracting and measuring the flow rate of an extracted sample of the exhaust comprising a second subsonic venturi restriction, and means for controlling the flow rate of the exhaust through said first subsonic venturi restriction and the flow rate of the extracted sample through said second subsonic venturi restriction for obtaining proportional sampling.

2. An apparatus as recited in claim 1, wherein said first and second subsonic venturi restrictions have substantially the same throat pressure for a predetermined ratio of the flow rate of the exhaust through the throat of said first subsonic venturi restriction to the flow rate of the extracted sample through the throat of said second subsonic venturi restriction.

3. An apparatus as recited in claim 2, wherein the ratio of the cross sectional area of said first subsonic venturi restriction to the cross sectional area of the second subsonic venturi restriction is substantially equal to the ratio of the flow rate of the exhaust through the throat of said first subsonic venturi restriction to the flow rate of the extracted sample through the throat of said second subsonic venturi restriction.

4. An apparatus as recited in claim 2, further comprising a differential pressure measuring device for measuring the pressure differential between the exhaust in the throat of said first subsonic venturi restriction and the extracted sample in the throat of said second subsonic venturi restriction and transmitting a correction signal to said sample flow rate controlling means for adjusting the flow rate of the extracted sample so that the pressure differential between the exhaust in the throat of said first subsonic venturi restriction and the extracted sample in the throat of said second subsonic venturi restriction is maintained at minimum value.

5. An apparatus as recited in claim 1, further comprising a temperature measuring device and a first pressure measuring device for measuring the temperature and pressure respectively of the exhaust upstream of said first and second subsonic venturi restrictions, a second pressure measuring device for measuring the pressure at the throat of said first subsonic venturi restriction and a third pressure measuring device for measuring the pressure at the throat of said second subsonic venturi restriction.

6. An apparatus as recited in claim 5, further comprising a control unit for computing the flow rates of the exhaust and the extracted sample based on signals received from said temperature measuring device and said first, second, and third pressure measuring devices.

7. An apparatus as recited in claim 1, wherein the velocity of the exhaust in proximity to the inlet of said second subsonic venturi restriction is substantially equal to the velocity of the extracted sample at the inlet of said second subsonic venturi restriction so as to provide isokinetic sampling.

8. A method for sampling the emission content of exhaust from an exhaust source comprising the steps of establishing a flow of exhaust in a flow confining path, measuring the flow rate of the exhaust using a first subsonic venturi restriction, extracting and measuring the flow rate of an extracted sample of the exhaust using a second subsonic venturi restriction, and controlling the flow rate of the exhaust through said first subsonic venturi restriction and the flow rate of the extracted sample through said second subsonic venturi restriction to obtain proportional sampling.

9. A method as recited in claim 8, further comprising the step of maintaining substantially the same throat pressure in said first and second subsonic venturi restrictions for a predetermined ratio of the flow rate of the exhaust through the throat of said first subsonic venturi restriction to the flow rate of the extracted sample through the throat of said second subsonic venturi restriction.

* * * * *